(12) United States Patent
Zhao et al.

(10) Patent No.: US 11,504,079 B2
(45) Date of Patent: Nov. 22, 2022

(54) HYBRID ACTIVE MATRIX FLAT PANEL DETECTOR SYSTEM AND METHOD

(71) Applicant: The Research Foundation for The State University of New York, Albany, NY (US)

(72) Inventors: Wei Zhao, East Setauket, NY (US); James Scheuermann, Katonah, NY (US); Adrian Howansky, Centereach, NY (US); Rick Lubinsky, Port Jefferson Station, NY (US); Amirhossein Goldan, Stony Brook, NY (US); Jann Stavro, East Setauket, NY (US)

(73) Assignee: The Research Foundation for The State University of New York, Albany, NY (US)

( * ) Notice: Subject to any disclaimer, the term of this patent is extended or adjusted under 35 U.S.C. 154(b) by 0 days.

(21) Appl. No.: 16/464,888

(22) PCT Filed: Nov. 30, 2017

(86) PCT No.: PCT/US2017/063851
§ 371 (c)(1),
(2) Date: May 29, 2019

(87) PCT Pub. No.: WO2018/102497
PCT Pub. Date: Jun. 7, 2018

(65) Prior Publication Data
US 2019/0388042 A1 Dec. 26, 2019

Related U.S. Application Data

(60) Provisional application No. 62/516,923, filed on Jun. 8, 2017, provisional application No. 62/428,190, filed on Nov. 30, 2016.

(51) Int. Cl.
*A61B 6/00* (2006.01)
*G01T 1/20* (2006.01)
(Continued)

(52) U.S. Cl.
CPC .......... *A61B 6/4233* (2013.01); *G01T 1/2018* (2013.01); *G01T 1/246* (2013.01); *H01L 27/14612* (2013.01); *H01L 27/14676* (2013.01)

(58) Field of Classification Search
CPC ..... A61B 6/4233; G01T 1/2018; G01T 1/246; G01T 1/24; G01T 1/20; H01L 27/14612; H01L 27/14676; H01L 27/1464
See application file for complete search history.

(56) References Cited

U.S. PATENT DOCUMENTS

| 4,363,969 A | 12/1982 | Ong |
| 5,195,118 A | 3/1993 | Nudelman et al. |

(Continued)

FOREIGN PATENT DOCUMENTS

| CN | 103339527 A | 10/2013 |
| CN | 113192991 A | 7/2021 |

(Continued)

OTHER PUBLICATIONS

Supplementary Partial Extended European Search Report dated Aug. 13, 2020 received in European Application No. 17 87 6356.1.
(Continued)

*Primary Examiner* — Christine S. Kim
(74) *Attorney, Agent, or Firm* — Scully, Scott, Murphy & Presser, P.C.

(57) ABSTRACT

A hybrid radiation imaging sensor includes a low x-ray attenuating substrate, a photoconductor disposed over the substrate, and a scintillator disposed over the photoconductor. By combining direct x-ray conversion to electron-hole
(Continued)

pairs in the photo-conductor with indirect conversion of x-rays downstream of the photoconductor within the scintillator, improved x-ray imaging can be attained through an electronic readout located upstream of both the photoconductor and the scintillator without the need for excessive x-ray dosing.

16 Claims, 5 Drawing Sheets

(51) Int. Cl.
*G01T 1/24* (2006.01)
*H01L 27/146* (2006.01)

(56) References Cited

U.S. PATENT DOCUMENTS

| | | | |
|---|---|---|---|
| 5,196,702 A | 3/1993 | Tsuji et al. | |
| 5,198,673 A * | 3/1993 | Rougeot | G01T 1/2018 250/370.09 |
| 5,306,907 A | 4/1994 | Nudelman et al. | |
| 5,381,014 A | 1/1995 | Jeromin et al. | |
| 5,567,929 A | 10/1996 | Ouimette | |
| 5,650,626 A | 7/1997 | Trauernicht et al. | |
| 5,886,359 A | 3/1999 | Bringley et al. | |
| 5,994,157 A | 11/1999 | Aggas et al. | |
| 6,020,590 A | 2/2000 | Aggas et al. | |
| 6,078,643 A | 6/2000 | Vogelsong et al. | |
| 6,243,441 B1 | 6/2001 | Zur | |
| 6,310,351 B1 | 10/2001 | Zur | |
| 6,310,358 B1 | 10/2001 | Zur | |
| 6,326,625 B1 | 12/2001 | Zur | |
| 6,373,062 B1 | 4/2002 | Ghelmansarai | |
| 6,396,046 B1 | 5/2002 | Possin et al. | |
| 6,784,433 B2 | 8/2004 | Zur | |
| 6,864,484 B1 | 3/2005 | Zur | |
| 6,900,442 B2 | 5/2005 | Zur | |
| 6,946,660 B2 | 9/2005 | El-Hanany et al. | |
| 6,982,425 B1 | 1/2006 | Rougeot et al. | |
| 7,081,628 B2 | 7/2006 | Granfors et al. | |
| 7,105,828 B2 * | 9/2006 | Unger | G01T 1/2018 250/370.06 |
| 7,312,458 B2 | 12/2007 | Blevis | |
| 7,488,966 B2 | 2/2009 | Noda et al. | |
| 7,501,631 B2 | 3/2009 | Mandelkern et al. | |
| 7,723,692 B2 | 5/2010 | Miyake et al. | |
| 7,745,798 B2 | 6/2010 | Takahashi | |
| 7,956,332 B2 | 6/2011 | Burr et al. | |
| 8,253,212 B2 | 8/2012 | Wronski et al. | |
| 8,624,197 B2 | 1/2014 | Marcovici | |
| 8,759,781 B2 | 6/2014 | Lee et al. | |
| 8,836,069 B2 | 9/2014 | Karim et al. | |
| 9,401,383 B2 | 7/2016 | Karim | |
| 9,660,115 B2 | 5/2017 | Goldan et al. | |
| 9,698,193 B1 | 7/2017 | Karim et al. | |
| 9,784,693 B2 | 10/2017 | Karim et al. | |
| 10,466,370 B1 | 11/2019 | Lee | |
| 10,468,450 B2 | 11/2019 | Karim | |
| 10,514,471 B2 | 12/2019 | Karim et al. | |
| 10,690,787 B2 | 6/2020 | Lee | |
| 2002/0079458 A1 * | 6/2002 | Zur | H01L 27/14676 250/370.11 |
| 2003/0010923 A1 * | 1/2003 | Zur | G01T 1/2018 348/E5.086 |
| 2004/0146138 A1 | 7/2004 | Jiao | |
| 2006/0054835 A1 | 3/2006 | Rowlands et al. | |
| 2007/0075252 A1 * | 4/2007 | Misawa | H01L 27/307 250/370.11 |
| 2007/0080300 A1 | 4/2007 | Mandelkern et al. | |
| 2007/0099116 A1 | 5/2007 | Miyake | |
| 2007/0125953 A1 | 6/2007 | Miyake et al. | |
| 2008/0240339 A1 * | 10/2008 | Du | G01T 1/20 378/5 |
| 2009/0159806 A1 | 6/2009 | Imai | |
| 2010/0127279 A1 | 5/2010 | Takahashi | |
| 2010/0181487 A1 | 7/2010 | Wronski et al. | |
| 2010/0320391 A1 | 12/2010 | Antonuk | |
| 2011/0001052 A1 | 1/2011 | Struye | |
| 2011/0215250 A1 | 9/2011 | Ohta et al. | |
| 2012/0049075 A1 | 3/2012 | Nariyuki | |
| 2012/0119097 A1 | 5/2012 | Nishino et al. | |
| 2012/0241629 A1 | 9/2012 | Kuwabara | |
| 2013/0082264 A1 * | 4/2013 | Couture | G01T 1/2018 257/59 |
| 2013/0126743 A1 | 5/2013 | Iwakiri et al. | |
| 2013/0320221 A1 | 12/2013 | Ghelmansarai | |
| 2015/0060677 A1 * | 3/2015 | Hackenschmied | G01T 1/247 250/366 |
| 2015/0162384 A1 * | 6/2015 | Couture | H01L 27/308 257/40 |
| 2015/0263061 A1 | 9/2015 | Karim | |
| 2015/0287760 A1 | 10/2015 | Karim | |
| 2016/0161426 A1 | 6/2016 | Wober | |
| 2017/0045629 A1 | 2/2017 | Antonuk | |
| 2018/0106910 A1 * | 4/2018 | Verbakel | G01T 1/24 |
| 2018/0240848 A1 * | 8/2018 | Heo | C09K 11/664 |
| 2018/0277608 A1 * | 9/2018 | Lifka | H01L 51/441 |
| 2019/0113466 A1 * | 4/2019 | Karim | A61B 6/484 |
| 2019/0388042 A1 | 12/2019 | Zhao et al. | |

FOREIGN PATENT DOCUMENTS

| | | |
|---|---|---|
| CN | 113491016 A | 10/2021 |
| DE | 696 35 303 T2 | 7/2006 |
| DE | 10 2011 080 892 B3 | 2/2013 |
| EP | 0 747 970 B1 | 12/1996 |
| EP | 0 955 664 A1 | 11/1999 |
| EP | 1 022 586 A1 | 7/2000 |
| JP | 7-63859 A | 3/1995 |
| JP | 7-235652 A | 9/1995 |
| JP | 11-500263 A | 1/1999 |
| JP | 11-211832 A | 8/1999 |
| JP | 2000-132662 A | 5/2000 |
| JP | 2000-513443 A | 10/2000 |
| JP | 2003-194950 A | 7/2003 |
| JP | 2007-150277 A | 6/2007 |
| JP | 2007-163250 A | 6/2007 |
| JP | 2007-169647 A | 7/2007 |
| JP | 2007-170908 A | 7/2007 |
| JP | 2007-170954 A | 7/2007 |
| JP | 2008-71961 A | 3/2008 |
| JP | 2008-270622 A | 11/2008 |
| JP | 2008-277600 A | 11/2008 |
| JP | 2009-135212 A | 6/2009 |
| JP | 2010-27834 A | 2/2010 |
| JP | 2011-22132 A | 2/2011 |
| JP | 2011-137804 A | 7/2011 |
| JP | 2011-227044 A | 11/2011 |
| JP | 2012-26932 A | 2/2012 |
| JP | 2012-107886 A | 6/2012 |
| JP | 5010190 B2 | 6/2012 |
| JP | 2012-141297 A | 7/2012 |
| JP | 2012-168009 A | 9/2012 |
| JP | 2012-177623 A | 9/2012 |
| JP | 2012-200455 A | 10/2012 |
| JP | 2012-233780 A | 11/2012 |
| JP | 5070031 B2 | 11/2012 |
| JP | 5077921 B2 | 11/2012 |
| JP | 5129473 B2 | 11/2013 |
| JP | 2014-90863 A | 5/2014 |
| JP | 2014-090863 A | 5/2014 |
| JP | 5703044 B2 | 4/2015 |
| JP | 2017-501388 A | 1/2017 |
| JP | 2018-530169 A | 10/2018 |
| KR | 2000-0016788 A | 3/2000 |
| KR | 10-2012-0027541 A | 3/2012 |
| KR | 10-1539571 A | 7/2015 |
| KR | 10-2017-0067452 A | 6/2017 |
| KR | 10-2021-0003281 A | 1/2021 |
| WO | 94/20976 A1 | 9/1994 |
| WO | 00/68710 A2 | 11/2000 |
| WO | 2010/121386 A1 | 10/2010 |

(56) References Cited

FOREIGN PATENT DOCUMENTS

| WO | 2012/109729 A1 | 8/2012 |
| WO | 2013/156211 A1 | 10/2013 |
| WO | 2021/216075 A1 | 10/2021 |

OTHER PUBLICATIONS

International Search Report dated Mar. 5, 2018 issued in PCT/US2017/063851.
Japanese Notice of Reasons for Rejection dated Nov. 8, 2021 received in Japanese Application No. 2019-517340, together with an English-language translation.
Australian Examination Report dated Feb. 1, 2022 received in Australian Application No. 2017367615.
European Communication dated Mar. 9, 2022 received in European Application No. 17 876 356.1.
Korean Office Action dated Apr. 28, 2022 received in Korean Patent Application No. 10-2019-7015312, together with an English-language translation.

* cited by examiner

HYBRID ACTIVE MATRIX FLAT PANEL DETECTOR SYSTEM AND METHOD

CROSS-REFERENCE TO RELATED APPLICATIONS

This application claims the benefit of U.S. Provisional Application No. 62/428,190 filed on Nov. 30, 2016 and U.S. Provisional Application No. 62/516,923 filed on Jun. 8, 2017, the entire contents of each of which is incorporated herein by reference.

BACKGROUND

The present application relates generally to an apparatus and methods for detecting ionizing radiation, and more specifically to a hybrid sensor for x-ray imaging.

The field of x-ray imaging experienced a "digital revolution" in the early 2000s with the proliferation of digital radiography (DR) systems, which are based on active matrix flat panel imagers (AMFPI). Since then, rapid development and clinical translation of large-area AMFPI has occurred based on amorphous silicon (a-Si) active matrix technology. Because of their compact size, rapid image readout and excellent image quality, AMFPI is being used not only for traditional x-ray imaging modalities such as general radiography and fluoroscopy, but also in tomographic imaging applications including cone beam computed tomography (CBCT) and digital tomosynthesis.

Digital x-ray systems provide visible representations of x-ray patterns for dental and medical applications, among others, including fluoroscopy, cone beam computed tomography (CBCT) and cardiac imaging. Conventional x-ray systems typically rely on the direct conversion of x-rays to charge carriers (e.g., electron-hole pairs) or the indirect conversion of x-rays to charge carriers via an intermediate state, such as optical photons (e.g., visible light).

Referring to FIG. 1A, direct conversion approaches typically use an x-ray sensitive photoconductor 12 such as a layer of amorphous selenium (a-Se) disposed over a solid state element including an array of pixel electrodes 14 and thin film transistors (TFTs) or diodes 16, each coupled to a storage capacitor 18. A scanning control system 22 and multiplexer 24 are configured to accumulate and electronically address image data.

In a direct conversion detector 10, x-rays 11 interact in the photoconductor 12 where they are converted to electron hole pairs (EHPs) and digitized through the readout electronics (TFT or CMOS). As shown in the illustrated example, a bias electrode 20 may overlie the photoconductor layer 12.

The direct conversion detector 10 benefits from high spatial resolution due to the intrinsic resolution of the photoconductor 12. However, for high energy applications, such as fluoroscopy, CBCT, and cardiac imaging, most photoconductors do not have sufficient quantum efficiency to fully attenuate incident x-rays. A photoconductor comprising a 1000 µm thick layer of a-Se, for example, exhibits limited quantum efficiency, resulting in a low signal-to-noise ratio. Moreover, poor charge transport within such a thick photoconductor layer may result in ghosting, lag, and/or loss of signal. Although adequate signal may be achieved by increasing the quantity of radiation administered, as will be appreciated, it is desirable to achieve diagnostic images having sufficient contrast and brightness while minimizing the x-ray exposure dose to a patient.

As a result, high energy applications tend to use an indirect detector, which has better quantum efficiency.

Referring to FIG. 1B, an indirect conversion detector 30 uses a scintillator or phosphor screen 32 to first convert x-rays 11 to optical photons, which are then absorbed in a photodiode 34 and digitized through the electronic readout. However, while the quantum efficiency of an indirect conversion detector 30 typically exceeds that of a direct conversion detector 10, optical blur within the scintillator may result in inferior spatial resolution relative to that which is achievable with a direct conversion detector.

The sensitivity and maximum signal-to-noise ratio (SNR) of indirect detectors, for example, are limited by their optical photon conversion efficiency. Low conversion efficiency not only decreases detector sensitivity, but also adds noise (e.g., secondary quantum noise) to acquired images. This noise can inhibit the resolution of fine details. In view of the foregoing, it will be appreciated that x-ray imaging techniques that are based on direct or indirect radiation conversion provide an inadequate combination of efficiency and resolution.

SUMMARY

Notwithstanding recent developments, there is a need for improved imaging sensors for x-ray applications that provide adequate contrast and brightness, for example, without requiring an excessive dose of radiation.

Disclosed herein is a hybrid detector, such as a hybrid active matrix flat panel detector system and method for implementing the system, that improves x-ray detector performance for radiological imaging, including fluoroscopy and CBCT. Various embodiments provide improved image quality without requiring an increased dose to be administered to a patient.

In accordance with various embodiments, a radiation imaging sensor includes a low x-ray attenuating substrate, a photoconductive element disposed over the substrate, and a scintillator disposed over the photoconductive element. The photoconductive element may include a layer of amorphous selenium (a-Se), for example.

A further example radiation imaging sensor includes, from bottom to top, a low x-ray attenuating substrate, a pixel electrode array, a first charge blocking layer, a photoconductive element, a second charge blocking layer, a transparent conductive electrode, and a scintillator optically coupled to the photoconductive element.

The hybrid detector utilizes direct interactions within the photoconductor as well as indirect interactions from the scintillator, and thereby combines the high spatial resolution of an amorphous selenium direct detector with the high quantum efficiency of an indirect detector.

According to further embodiments, a method for imaging x-ray radiation includes exposing a radiation imaging sensor comprising a photoconductive element and a scintillator to x-ray radiation, and directly generating charge carriers within the photoconductive element in response to absorption of a first portion of the radiation by the photoconductive element, wherein a second portion of the radiation passes through the photoconductive element.

The method further includes generating optical photons within the scintillator in response to absorption of the second portion of the radiation by the scintillator. Charge carrier are generated within the photoconductive element in response to absorption of the optical photons by the photoconductive element.

A method of forming a radiation imaging sensor includes forming a photoconductive element over a low x-ray attenuating substrate, and forming a scintillator over the photoconductive element. In certain embodiments, a photoelectric conversion layer may be formed over the photoconductive element prior to forming the scintillator.

BRIEF DESCRIPTION OF SEVERAL VIEWS OF THE DRAWINGS

The following detailed description of specific embodiments of the present application can be best understood when read in conjunction with the following drawings, where like structure is indicated with like reference numerals and in which.

DETAILED DESCRIPTION

Figure 1B:
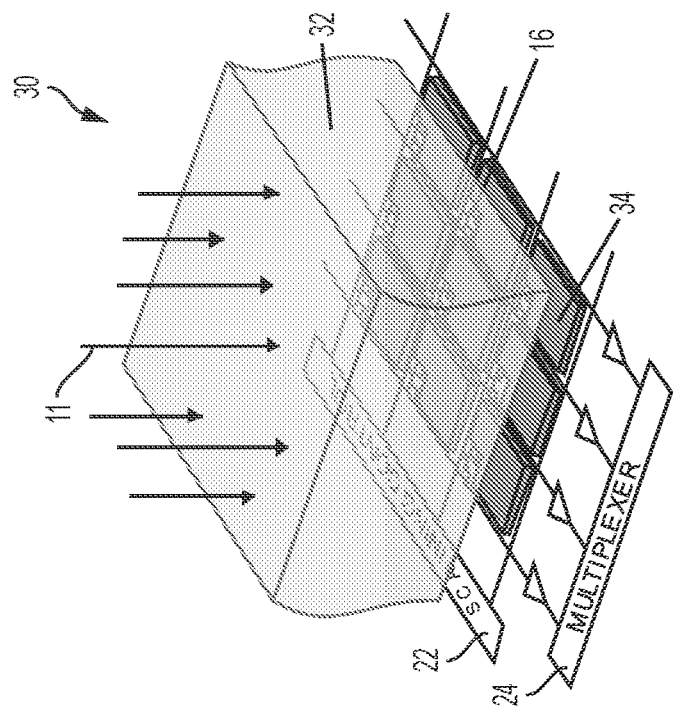
FIG. 1B is a schematic diagram of a conventional x-ray detector, where x-rays are initially converted to optical photons in a scintillator, followed by conversion of the optical photons to electron-hole pairs in a photodiode.
Figure 1A:
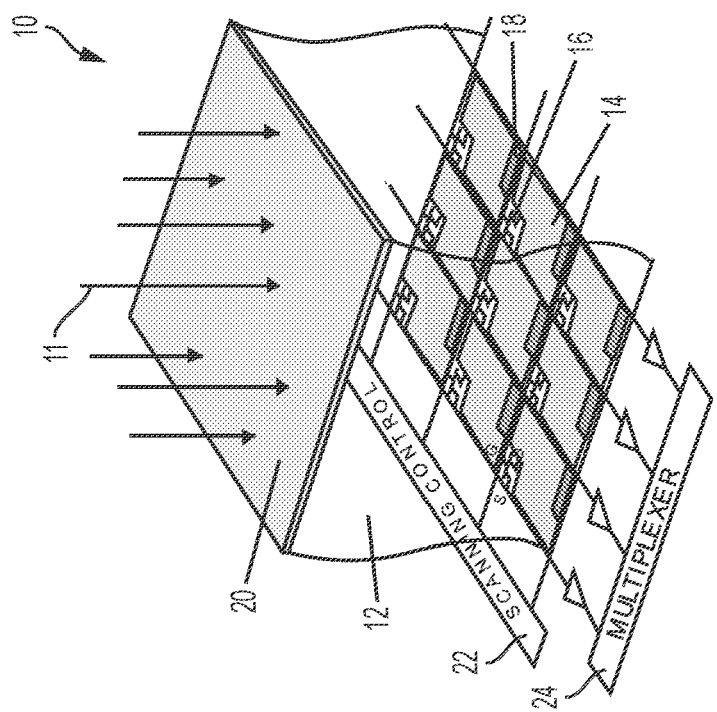
FIG. 1A is a schematic diagram of a conventional x-ray detector in which a single photoconductive layer converts x-rays directly to electron-hole pairs.

Reference will now be made in greater detail to various embodiments of the subject matter of the present application, some embodiments of which are illustrated in the accompanying drawings. The same reference numerals will be used throughout the drawings to refer to the same or similar parts.

Figure 2:
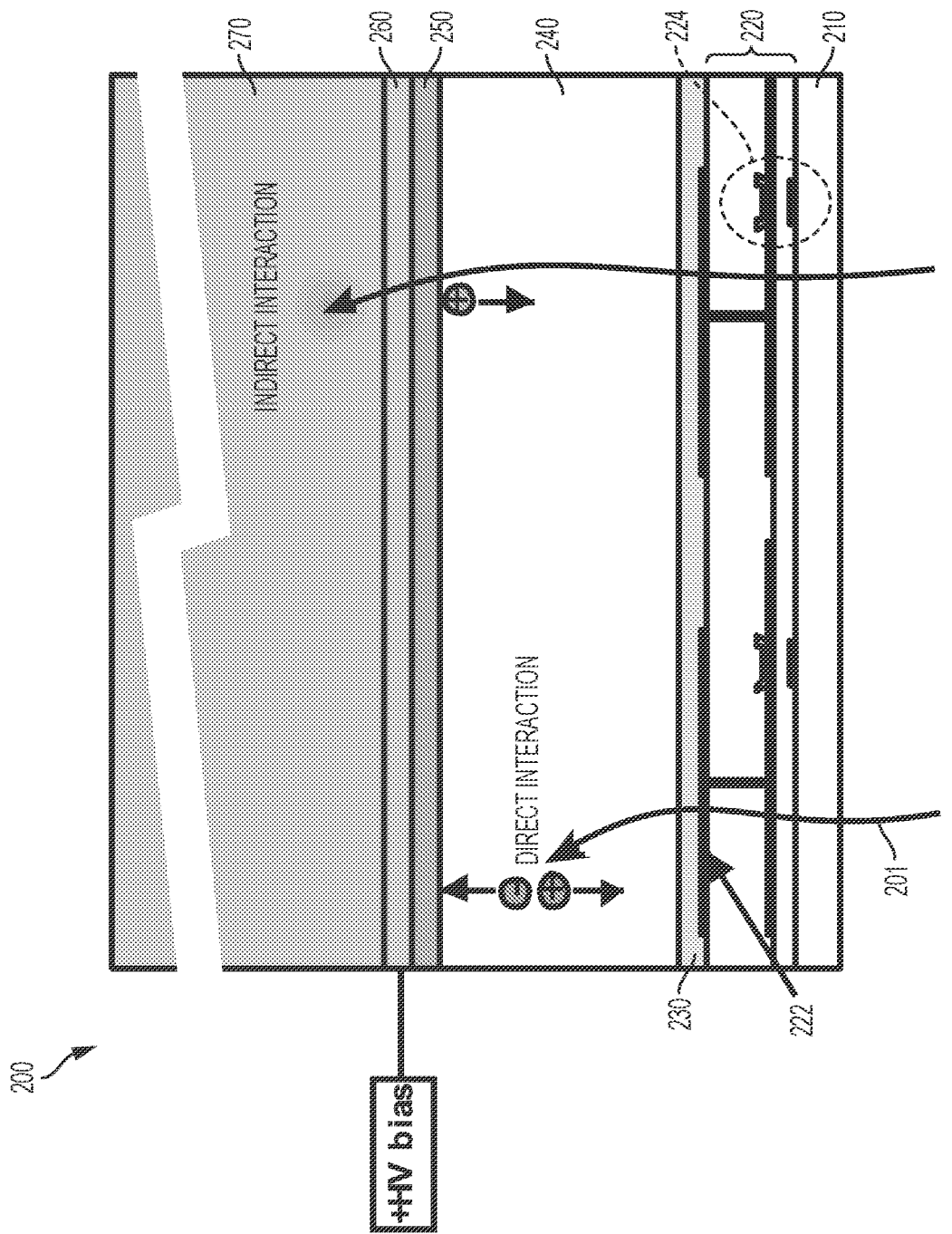
FIG. 2 is a schematic diagram of a hybrid x-ray imaging sensor according to various embodiments.

Referring to FIG. 2, a hybrid x-ray imaging sensor 200 according to various embodiments includes a low x-ray attenuating substrate 210, an electronic readout 220, a first charge blocking layer 230, a photoconductive element 240, a second charge blocking layer 250, a transparent conductive electrode 260, and a scintillator 270 optically coupled to the photoconductive element 240.

The low x-ray attenuating substrate 210, which may provide mechanical support for the overlying layers and structures, may be a glass substrate having a thickness of 20 to 100 microns. For instance, substrate 210 may be a low barium glass substrate or a polymer substrate. A low x-ray attenuating substrate allows x-rays to pass through to the photoconductive element 240 and the scintillator 270. As used herein, "low x-ray attenuating" means that the transmission of x-rays through the substrate 210 is at least 75%, e.g., 75, 80, 90, 95, 97 or 98%, including ranges between any of the foregoing values.

In certain embodiments, the low x-ray attenuating substrate 210 may be a flexible substrate. For instance, any thin flexible glass may be used as a substrate. Suitable flexible substrates may be bent to a radius of curvature of 3 to 4 cm. An electronic readout 220 may be formed over the substrate 210.

The electronic readout 220 may include an array of pixel electrodes 222 each coupled to a thin film transistor 224 having a source region (S), drain region (D) and gate (G). The array is partitioned into a plurality of individual cells arranged rectilinearly in rows and columns. Each thin film transistor 224 may be electrically connected to a storage capacitor. According to various embodiments, the electronic readout 220 is x-ray transparent and radiation insensitive. The electronic readout 220 is disposed proximate to the substrate 210, i.e., between the substrate and the photoconductive element 240, such that sampling occurs near the x-ray entrance plane of the sensor. With such a geometry, the spatial resolution of the scintillator is improved.

First charge blocking layer 230, which is located between the photoconductive element 240 and the electronic readout 220 is configured to prevent the passage of charge, e.g., electrons, between the photoconductive element 240 and the electronic readout 220, i.e., pixel electrodes 222. First charge blocking layer 230 may include a dielectric materials such as silicon dioxide or silicon nitride, for example, and may be formed using a vacuum deposition technique such as physical vapor deposition (PVD), including thermal evaporation or sputtering.

The photoconductive element 240 may include a layer of amorphous selenium (a-Se) and may have a thickness of 50 to 1000 microns, e.g., 50, 100, 200, 400, 600, 800 or 1000 microns, including ranges between any of the foregoing values. In certain embodiments, an amorphous selenium photoconductive element 240 may include one or more dopants, such as arsenic or chlorine. In lieu of amorphous selenium, the photoconductive element 240 may include other photoconductive materials such as cadmium telluride (CdTe), lead iodide ($PbI_2$), lead (II) oxide (PbO), mercuric iodide ($HgI_2$) or a perovskite material, such as lead zirconate titanate (PZT) or barium strontium titanate (BST). In certain embodiments, the photoconductive element may include quantum dots of one or more such materials.

A photoconductive element 240 may be a photoconductive thin film formed by any suitable technique, such as thermal evaporation, sputtering, or a solution-based process such as a sol gel process. One or more sintering steps may be used to densify a photoconductive thin film.

The second charge blocking layer 250, which is located between the photoconductive element and the scintillator 270, is configured to prevent the passage of charge, e.g., holes, between the photoconductive element 240 and high voltage (HV) electrode 260, while allowing optical radiation emitted from the scintillator 270 to be transmitted therethrough into the photoconductive element 240. An example second charge blocking layer 250 includes a dielectric material such as silicon dioxide or silicon nitride.

As used herein, the compounds silicon dioxide and silicon nitride have compositions that are nominally represented as $SiO_2$ and $Si_3N_4$, respectively. The terms silicon dioxide and silicon nitride refer to not only these stoichiometric compositions, but also to oxide and nitride compositions that deviate from the stoichiometric compositions.

The photoconductive element 240 may be biased with high voltage electrode 260, and separated from the pixel electrodes 222 and the high voltage electrode 260 by first and second charge blocking layers 230, 250, respectively. High voltage electrode 260 may be a transparent conductive electrode, which permits optical transmission of photons from the scintillator 270 to the photoconductive element 240. An example transparent conductive electrode may include a conductive metal oxide such as indium tin oxide (ITO), or a conductive organic polymer such as poly(3,4-ethylenedioxythiophene) (PEDOT).

A scintillator screen 270 is configured to absorb x-ray radiation and convert the absorbed x-ray radiation to optical radiation. An example of a suitable material for scintillator 270 is un-doped or doped cesium iodide (CsI), e.g., thallium-doped cesium iodide (CsI:Tl), which has a peak emission at about 550 nm. Scintillators that emit at greater or lesser wavelengths can also be used. Scintillator 270 may emit blue light or green light, for example. Other example scintillating materials including bismuth germinate (BGO), lutetium orthosilicate (LSO), lutetium yttrium orthosilicate (LYSO) and scintillating glasses.

Scintillators that emit in blue wavelengths include but are not limited to barium fluorohalides (e.g., barium fluorobromide, barium fluorochloride, barium fluoroiodide, etc.) and calcium tungstate. Blue light has high optical quantum efficiency in a-Se (>80%), which allows a-Se to be coupled directly to a blue scintillator.

Example scintillators 270 that emit green wavelengths include thallium-doped cesium iodide (CsI:Tl) and terbium-doped gadolinium oxysulfide (GOS). Because the optical quantum efficiency of scintillators that emit in the green can be less than 20%, in certain embodiments an additional green-sensitive photoconductive layer (not shown) may be included between the a-Se layer 240 and the high voltage (HV) electrode 260. The additional photoconductive layer may include, for example, tellurium-doped a-Se or other compound semiconductors such as cadmium selenide.

As will be appreciated, the scintillator composition and geometry (e.g., thickness) may be chosen for a particular application. In certain embodiments, the effective EHP creation energy ($W\pm$) of scintillator 270 matches that of a-Se ($W\pm=50$) so that all x-rays are counted equally.

During a radiography session, an x-ray beam impinges on a patient and is imagewise altered as it passes through the patient's anatomy. The spatially-altered radiation containing information relating to the patient's anatomy impinges on the imaging sensor 200.

During operation, x-rays 201 are incident on sensor 200 through the substrate 210 and through the electronic readout (TFT array) 220. For example, the x-rays may pass through the photoconductor layer 240 where a first portion of the x-rays are attenuated and directly converted to electron-hole pairs. The direct conversion is shown schematically in FIG. 2.

A second portion of the x-rays may pass through the photoconductor layer 240. The second portion of the x-rays may be absorbed by scintillator 270, and converted to optical photons. The optical photons are, in turn, converted to electron-hole pairs in the photoconductor layer 240.

Thus, in various embodiments, incident x-rays 201 are absorbed and converted to electron-hole pairs via both direct interactions in the photoconductor 240 and indirect interactions using the scintillator 270. In certain embodiments, the photoconductor 240 is configured to sense both x-rays and optical photons. This hybrid structure allows spatial resolution and dose efficiency improvements beyond those which are achievable with direct or indirect detectors alone.

Referring still to FIG. 2, incident x-rays 201 interact with the photoconductor 240 prior to interacting with the scintillator 270. A first portion of the x-rays, e.g., lower energy x-rays, which possess higher radiographic contrast than higher energy x-rays, may be absorbed by the photoconductor 240 and converted directly into electron-hole pairs.

A second portion of the x-rays, e.g., higher energy x-rays that do not interact with the photoconductor 240, may be absorbed by the scintillator 270, which has a higher stopping power (but lower spatial resolution) than the photoconductor 240. The indirect conversion of such higher energy x-rays to electron hole pairs may enhance the overall absorption efficiency of the detector.

In various embodiments, the a-Se photoconductor 240 is adapted to function as both a direct detector of x-rays and as a detector for optical photons. In accordance with various embodiments, the optical coupling and quantum efficiency of a-Se is used to achieve a well-matched signal gain between the x-rays absorbed in the scintillator and those absorbed in a-Se.

Figure 3B:
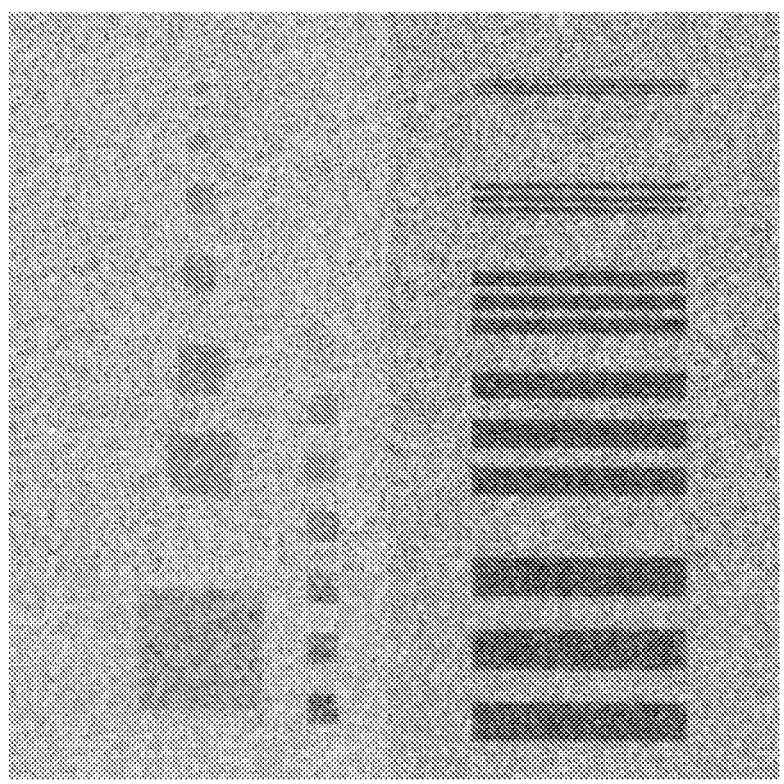
FIG. 3B shows an improved x-ray image produced using an exemplary hybrid imaging sensor.
Figure 3A:
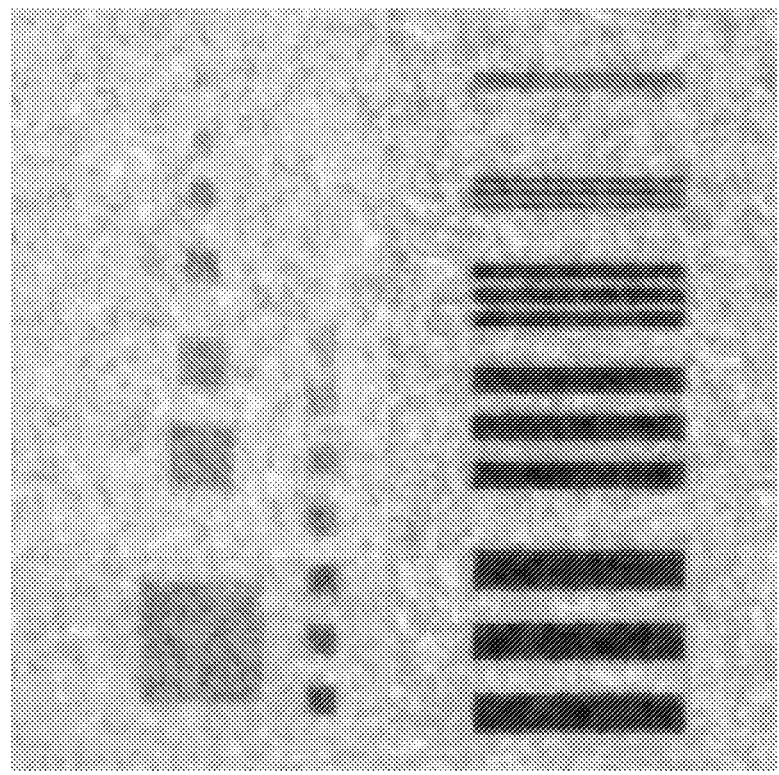
FIG. 3A shows a comparative x-ray image produced using a terbium-doped gadolinium oxysulfide indirect detector having a pixel pitch of 150 microns.

Improvements in imaging using the disclosed hybrid detector 200 can be appreciated with reference to FIG. 3A and FIG. 3B. Referring to FIG. 3A, shown is a simulated image derived using a comparative indirect detector. The phantom image of FIG. 3A is produced using a standard terbium-doped gadolinium oxysulfide (GOS) phosphor screen with a pixel pitch of 150 μm.

Referring to FIG. 3B, shown is the same simulated image derived using a hybrid detector as disclosed herein. The improvement in sharpness with the hybrid detector is evident. The contrast modulation of the 300 micron line group in the simulated phantom (second from bottom right) is improved by a factor of 3, for example.

Figure 4:
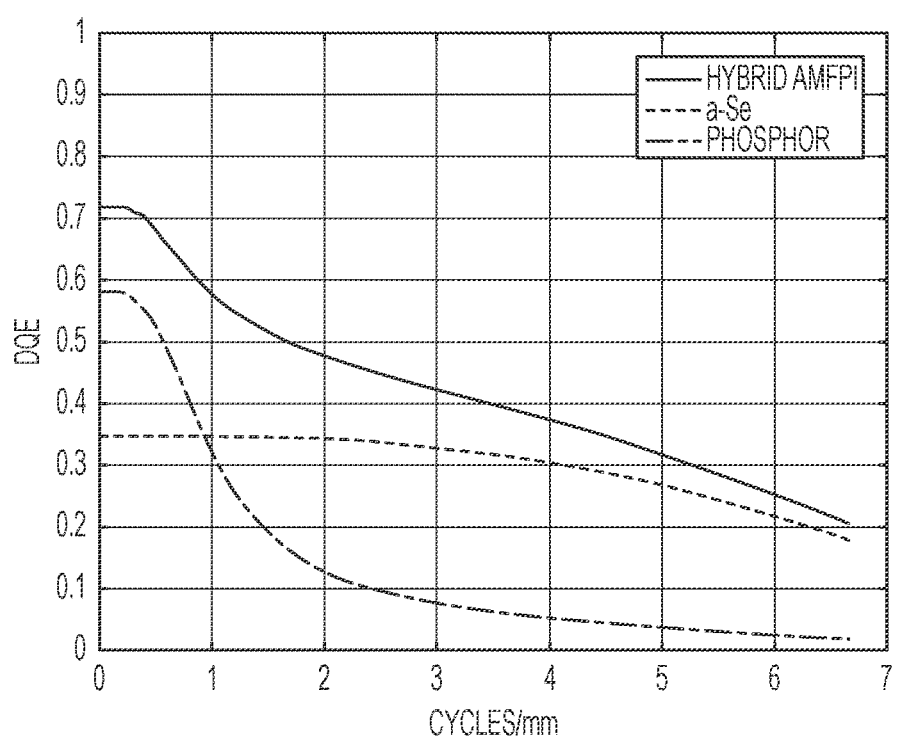
FIG. 4 is a plot of detective quantum efficiency versus spatial frequency for a hybrid AMFPI according to certain embodiments.

The improved imaging efficiency of a hybrid detector can be appreciated with reference to FIG. 4, which is a plot of detective quantum efficiency (DQE) versus spatial frequency for (A) a hybrid AMFPI as disclosed herein, (B) a comparative a-Se-based direct detector, and (C) a comparative phosphor-based indirect detector.

The detective quantum efficiency is a measure of the combined effects of the signal and noise performance of an imaging system. In medical radiography, the DQE describes how effectively an imaging system can produce an image with a high signal-to-noise ratio relative to an ideal detector. Referring to FIG. 4, it is readily apparent that the DQE for the hybrid AMFPI is greater than the DQE for either the direct or the indirect detector over a domain of 0 to 7 cycles/mm.

Figure 5:
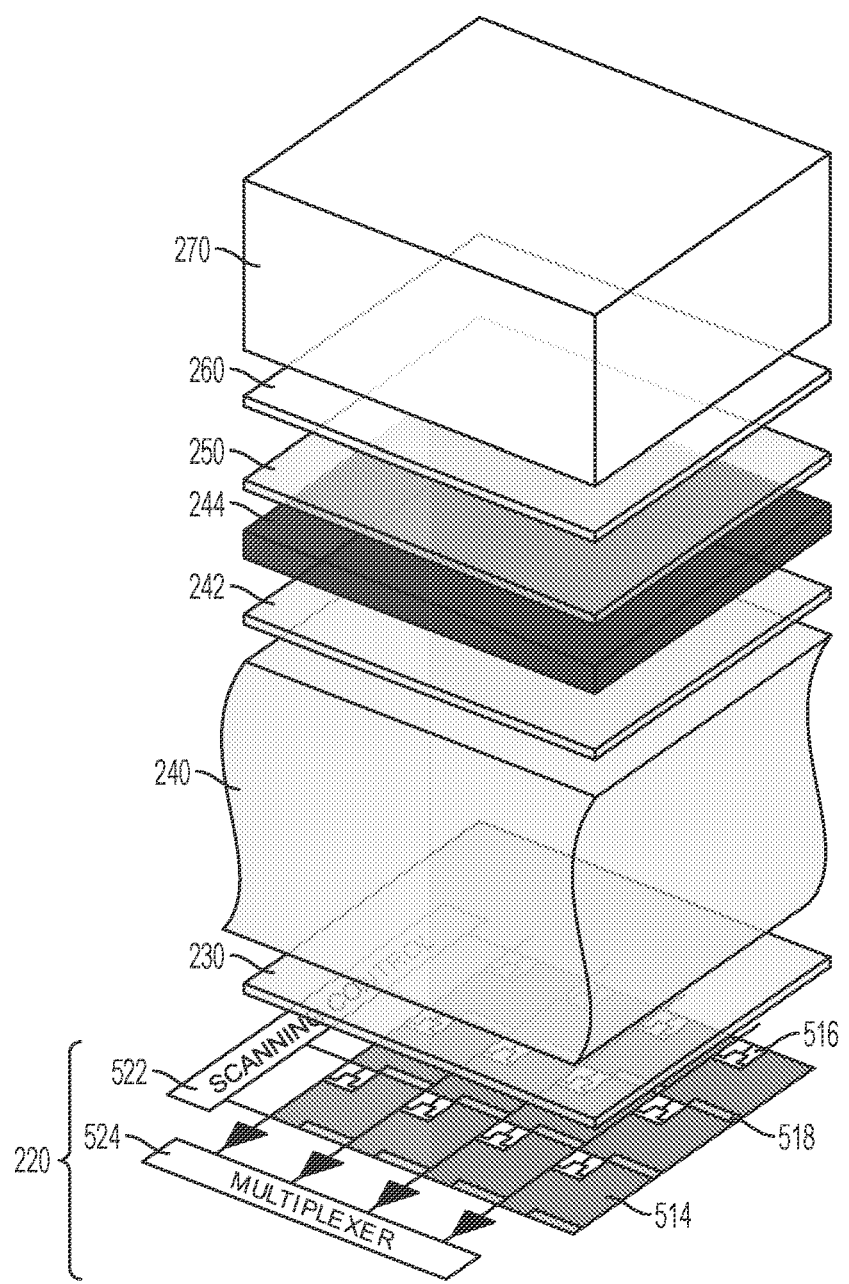
FIG. 5 is an exploded view of a hybrid x-ray imaging sensor including a photoelectric conversion layer according to various embodiments.

Referring to FIG. 5, a planar hybrid x-ray imaging sensor according to various embodiments includes, from bottom to top, an electronic readout 220, a first charge blocking layer 230, a photoconductive element 240, a buffer layer 242, a photoelectric conversion layer 244, a second charge blocking layer 250, a transparent conductive electrode 260, and a scintillator 270 optically coupled to the photoelectric conversion layer 244 and the photoconductive element 240.

Electronic readout 220 may include a solid state element having an array of pixel electrodes 514 and thin film transistors (TFTs) or diodes 516, for example, each coupled to a storage capacitor 518. A scanning control system 522 and multiplexer 524 are configured to accumulate and electronically address image data.

In the instant embodiment, a buffer layer 242 and a photoelectric conversion layer 244 are disposed between the photoconductive element 240 and the charge blocking layer 250. Buffer layer 242, which may comprise doped amorphous selenium, e.g., arsenic-doped amorphous selenium, is adapted to enhance the stability and inhibit the crystallization of the photoconductive element 240. In certain embodiments, buffer layer 242 may be omitted. The photoelectric conversion layer 244 may comprise cadmium selenide (CdSe) or cadmium sulfide (CdS), for example. In certain embodiments, the photoelectric conversion layer 244 is adapted to supplement the photoconductive element 240. During use, according to various embodiments, x-rays may be incident upon the upper surface (e.g., scintillator 270) or lower surface (e.g., electronic readout 220) of the planar, hybrid sensor of FIG. 5.

The various hybrid sensor architectures disclosed herein may be fabricated layer-by-layer using one or more conventional thin film deposition processes, such as sputtering, thermal evaporation, electron beam evaporation, or a solution-based deposition method. Referring again to FIG. 5, an example manufacturing process flow may include forming a photoconductive element 240 over an electronic readout 220. A photoconductive element 240 comprising amorphous selenium may be formed by evaporation. The photoconductive element 240 may serve as a conversion layer for converting x-rays to electronic charge and/or as a drift layer to transport photo-generated charge towards the electronic readout 220. In certain embodiments, a layer of doped selenium may be deposited, e.g., by evaporation, directly over the photoconductive element 240 to form a buffer layer 242. A photoelectric conversion layer 244 may be formed over the buffer layer 242, if present, or directly over the photoconductive element 240. The photoelectric conversion layer 244 may be formed, for example, by thermal evaporation, electron beam evaporation, sputtering or solution processing, e.g., by spin-coating liquid suspension of quantum dots. In certain embodiments, the photoelectric conversion layer 244 is formed at a deposition temperature of 30° C. or less. In certain applications the photoelectric conversion layer 244 is adapted to function as a charge blocking layer (e.g., hole blocking layer) to inhibit or prevent charge injection from an overlying electrode into the photoconductive element 240. In various embodiments, a charge blocking layer 250, such as layer of zinc oxide (ZnO), is formed over the photoelectric conversion layer 244. The charge blocking layer 250 may be formed at a deposition temperature of 30° C. or less by thermal evaporation, electron beam evaporation, sputtering or solution processing, e.g., using a liquid dispersion of colloidal ZnO particles or colloidal quantum dots. A transparent conductive electrode 260 may be formed over the charge blocking layer 250, and a scintillator 270 adapted to convert x-rays to photons, may be formed over the transparent conductive electrode 260.

Applicant has demonstrated that the combination of an indirect conversion x-ray flat panel imager with a high-efficiency photoelectric conversion layer 244 provides improved dynamic range and sensitivity, which are beneficial for digital radiography. The incorporation of a photoelectric conversion layer 244 between the photoconductive element 240 (e.g., a-Se) and the scintillator (e.g., CsI) may improve the optical photon conversion efficiency of the sensor.

Improved optical photon conversion efficiency provides practical advantages for various applications, including high signal-to-noise performance and a decrease in the negative impact of electronic noise in low-dose fluoroscopy.

As disclosed herein, a hybrid detector takes advantage of the merits of direct and indirect detectors while minimizing their respective shortcomings. Direct interaction of x-rays in selenium helps preserve image sharpness and overcomes electronic noise at high spatial frequencies. Although the x-ray signal from the scintillating layer is blurred compared to that in a-Se, its high absorption efficiency increases the total detector signal and improves low-dose performance.

The disclosed hybrid detectors exhibit improved dose efficiency compared to conventional direct conversion detectors, and better spatial resolution compared to conventional indirect conversion detectors. High absorption efficiency combined with higher spatial resolution results in better quantum efficiency and improved imaging, especially for fine detail and low contrast objects.

It will be appreciated that the disclosed sensor may be used with a variety of x-ray systems for diagnostic imaging, such as general radiography and mammography.

As used herein, the singular forms "a," "an" and "the" include plural referents unless the context clearly dictates otherwise. Thus, for example, reference to a "pixel electrode" includes examples having two or more such "pixel electrodes" unless the context clearly indicates otherwise.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that any particular order be inferred. Any recited single or multiple feature or aspect in any one claim can be combined or permuted with any other recited feature or aspect in any other claim or claims.

It will be understood that when an element such as a layer, region or substrate is referred to as being formed on, deposited on, or disposed "on" or "over" another element, it can be directly on the other element or intervening elements may also be present. In contrast, when an element is referred to as being "directly on" or "directly over" another element, no intervening elements are present.

While various features, elements or steps of particular embodiments may be disclosed using the transitional phrase "comprising," it is to be understood that alternative embodiments, including those that may be described using the transitional phrases "consisting" or "consisting essentially of," are implied. Thus, for example, implied alternative embodiments to a photodetector comprises amorphous selenium include embodiments where a photodetector consists essentially of amorphous selenium and embodiments where a photodetector consists of amorphous selenium.

It will be apparent to those skilled in the art that various modifications and variations can be made to the present invention without departing from the spirit and scope of the invention. Since modifications, combinations, sub-combinations and variations of the disclosed embodiments incorporating the spirit and substance of the invention may occur to persons skilled in the art, the invention should be construed to include everything within the scope of the appended claims and their equivalents.

What is claimed is:

1. A radiation imaging sensor, comprising:
   a low x-ray attenuating substrate;
   a photoconductive element disposed over the substrate;
   a scintillator disposed over the photoconductive element;
   a photoelectric conversion layer disposed between the photoconductive element and the scintillator, wherein the photoelectric conversion layer comprises tellurium-doped a-Se, cadmium selenide or cadmium sulfide, wherein the photoconductive element is disposed between the substrate and the photoelectric conversion layer; and
   a charge blocking layer between the photoelectric conversion layer and the scintillator, wherein an effective electron-hole pair (EHP) creation energy (W±) of the scintillator is substantially equal to an effective electron-hole pair (EHP) creation energy (W±) of the photoconductive element.

2. The radiation imaging sensor of claim 1, wherein the substrate is a flexible substrate.

3. The radiation imaging sensor of claim 1, further comprising a charge blocking layer between the substrate and the photoconductive element.

4. The radiation imaging sensor of claim 1, further comprising a pixel electrode array between the substrate and the photoconductive element.

5. The radiation imaging sensor of claim 1, further comprising a transparent conductive electrode between the photoconductive element and the scintillator.

6. A radiation imaging sensor, comprising, from bottom to top:
- a low x-ray attenuating substrate;
- a pixel electrode array comprising a plurality of pixel electrodes;
- a first charge blocking layer;
- a photoconductive element;
- a photoelectric conversion layer, wherein the photoelectric conversion layer comprises tellurium-doped a-Se, cadmium selenide or cadmium sulfide;
- a second charge blocking layer;
- a transparent conductive electrode; and
- a scintillator optically coupled to the photoconductive element, wherein the photoelectric conversion layer is between the photoconductive element and the scintillator.

7. The radiation imaging sensor of claim 6, further comprising a thin film transistor and a storage capacitor in electrical communication with each of the plurality of pixel electrodes.

8. The radiation imaging sensor of claim 6, wherein the photoconductive element comprises a material selected from the group consisting of amorphous selenium, cadmium telluride, lead iodide, lead (II) oxide, mercuric iodide, lead zirconate titanate and barium strontium titanate, and the scintillator comprises a material selected from the group consisting of cesium oxide, bismuth germinate, lutetium orthosilicate, lutetium yttrium orthosilicate, calcium tungstate, thallium-doped cesium iodide, terbium-doped gadolinium oxysulfide, a barium fluorohalide and a scintillating glass.

9. The radiation imaging sensor of claim 6, further comprising a buffer layer between the photoconductive element and the photoelectric conversion layer.

10. A method for imaging x-ray radiation, comprising:
- exposing a radiation imaging sensor comprising a photoconductive element and a scintillator to x-ray radiation;
- directly generating charge carriers within the photoconductive element in response to absorption of a first portion of the radiation by the photoconductive element, wherein a second portion of the radiation passes through the photoconductive element;
- generating optical photons within the scintillator in response to absorption of the second portion of the radiation by the scintillator; and
- indirectly generating charge carriers within the photoconductive element in response to absorption of the optical photons by the photoconductive element.

11. The method of claim 10, wherein the x-ray radiation enters the sensor through a low x-ray attenuating substrate.

12. The method of claim 11, further comprising forming a charge pattern on a pixel electrode array located between the low x-ray attenuating substrate and the photoconductive element.

13. The method of claim 10, wherein the photoconductive element absorbs the first portion of the ionizing radiation and senses the optical photons.

14. A method of forming a radiation imaging sensor comprising:
- forming a photoconductive element over a low x-ray attenuating substrate;
- forming a photoelectric conversion layer over the photoconductive element;
- forming a charge blocking layer over the photoelectric conversion layer;
- forming a transparent conductive electrode over the charge blocking layer; and
- forming a scintillator over the transparent conductive electrode, wherein an effective electron-hole pair (EHP) creation energy (W±) of the scintillator is substantially equal to an effective electron-hole pair (EHP) creation energy (W±) of the photoconductive element.

15. The method of claim 14, further comprising forming a buffer layer over the photoconductive element prior to forming the photoelectric conversion layer.

16. A radiation imaging sensor, comprising:
- a low x-ray attenuating substrate;
- a photoconductive element disposed over the substrate; and
- a scintillator disposed over the photoconductive element, wherein an effective electron-hole pair (EHP) creation energy (W±) of the scintillator is substantially equal to an effective electron-hole pair (EHP) creation energy (W±) of the photoconductive element.

* * * * *